(12) United States Patent
Raeder et al.

(10) Patent No.: US 8,430,722 B2
(45) Date of Patent: Apr. 30, 2013

(54) DEVICE FOR PROCESSING OR TREATING SURFACE BY MEANS OF A DRY ICE GRANULATE

(75) Inventors: Niels Raeder, Munich (DE); Rosa Rolstein, Munich (DE)

(73) Assignee: TQ-Systems GmbH, Seefeld (DE)

( * ) Notice: Subject to any disclaimer, the term of this patent is extended or adjusted under 35 U.S.C. 154(b) by 301 days.

(21) Appl. No.: 12/594,598

(22) PCT Filed: Apr. 7, 2008

(86) PCT No.: PCT/EP2008/054151
§ 371 (c)(1),
(2), (4) Date: Dec. 11, 2009

(87) PCT Pub. No.: WO2008/122625
PCT Pub. Date: Oct. 16, 2008

(65) Prior Publication Data
US 2010/0113576 A1  May 6, 2010

(30) Foreign Application Priority Data
Apr. 5, 2007 (EP) .................................... 07105772

(51) Int. Cl.
*B24C 3/02* (2006.01)
(52) U.S. Cl.
USPC ......... 451/99; 241/227; 241/DIG. 17; 451/90
(58) Field of Classification Search .................. 241/227, 241/230, 234, 231, DIG. 17; 451/38, 39, 451/40, 75, 99, 100, 101, 90
See application file for complete search history.

(56) References Cited

U.S. PATENT DOCUMENTS

| | | | | |
|---|---|---|---|---|
| 2,079,854 A | * | 5/1937 | Hartshorne | 502/80 |
| 4,707,951 A | * | 11/1987 | Gibot et al. | 451/99 |
| 5,319,946 A | * | 6/1994 | Manificat | 62/342 |
| 6,270,394 B1 | * | 8/2001 | Visaisouk et al. | 451/39 |
| 6,890,246 B2 | * | 5/2005 | Yamaharu | 451/99 |
| 7,112,120 B2 | * | 9/2006 | Rivir et al. | 451/38 |
| 2003/0073392 A1 | * | 4/2003 | Stratford et al. | 451/99 |

FOREIGN PATENT DOCUMENTS

| | | |
|---|---|---|
| DE | 102004057665 A1 | 6/2006 |
| EP | 1852221 A1 | 11/2007 |
| FR | 2576821 A | 8/1986 |

OTHER PUBLICATIONS

International Search Report from International Patent Application Publication No. WO2008/122625, mailed on Oct. 14, 2008, pp. 1-10.

* cited by examiner

*Primary Examiner* — Timothy V Eley
(74) *Attorney, Agent, or Firm* — Lisa V. Mueller; Michael Best & Friedrich LLP

(57) ABSTRACT

The invention relates to an apparatus for surface processing or surface treatment by means of dry ice granulate, with a reservoir for receiving a dry ice medium, in particular dry ice pellets, an inlet for the feed of a propellant medium, an outlet for the supply of a mixture of propellant medium and dry ice granulate to a blast gun, and an outflow chamber lying therebetween, there being arranged in the path between the reservoir and the outflow chamber a grinding mechanism, which is formed so as to comminute the dry ice medium to dry ice granulate with a particle size in a prescribed range, and a transport roll (4) being arranged between the grinding mechanism (3) and the outflow chamber (59), the transport roll (4) being operable with a variable speed so as to vary the quantity of the particles of the dry ice granulate per unit time. Furthermore, the invention relates to a corresponding method and the use of the method.

4 Claims, 5 Drawing Sheets

DEVICE FOR PROCESSING OR TREATING SURFACE BY MEANS OF A DRY ICE GRANULATE

RELATED APPLICATIONS

This application is filed under 35 USC §371 from PCT Patent Application No. PCT/EP2008/054151 filed on Apr. 7, 2008, which claims the benefit of EP Patent Application No. 071057723, filed on Apr. 5, 2007, the teachings and content of which are hereby incorporated by reference herein.

The present invention relates to an apparatus and a method for surface processing or surface treatment by means of dry ice granulate and furthermore to a use of the method for the treatment of surfaces and of biological tissue.

PRIOR ART

Dry ice or dry ice granulate consists, as known to the person skilled in the art, of carbon dioxide (in the trade customarily also referred to as carbonic acid) in a solid state, which is customarily available in the form of pellets in a size of approximately 3 mm.

From DE 10 2004 045 770 B3, as represented schematically in FIG. 1, an apparatus for blasting a surface with a mixture of propellant gas (transport air) and dry ice granulate is known, which works in accordance with the pressure jet principle or single-hose principle and which, by reference, is included in full in the present application.

The known apparatus comprises an inlet 6 for the propellant gas supply, which inlet 6 is connected to an outlet 22, to which a transport hose 8 for dispensing the mixture of propellant gas and dry ice granulate via a blast gun 9 with a Laval nozzle 10 is connectable.

The known apparatus furthermore comprises a metering device 20 for introducing the dry ice granulate into the flow path of the propellant gas, the metering device 20 comprising a metering disc 30 rotatable, by motor, around a central axis, which metering disc 30 is arranged between a plate-shaped inflow part 32 and a plate-shaped outflow part 34 and exhibits a multiplicity of receiving chambers 44, which, about a drive axis 41, are positionable in a first rotational position of the metering disc 30, so as to be aligned with a feed chamber 57 of the outflow part 34, and in a second rotational position of the metering disc 30, between an inflow chamber 71 of the inflow part 32 and an outflow chamber 59 of the outflow part 34. A conventional motor 36 with speed control 39 is provided for rotation of the metering disc 30.

The feed chamber 57 is connected to a funnel-shaped reservoir 1 for introducing dry ice granulate into the feed chamber 57, the reservoir being filled with conventional dry ice pellets 2, which, under the influence of gravity and with the assistance of a vibrator 86, can pass into the feed chamber 57. From the feed chamber 57, the pellets 2 pass, under the influence of gravity, into one of the receiving chambers 44 in the first rotational position and are then carried, by the rotation of the metering disc 30, into the second rotational position, so that they are carried in the throughflow direction 93 in the direction of the outlet 22 and to the blast gun 9 so as subsequently to impinge, pressure-loaded, on the surface 28 to be cleaned or treated.

The apparatus of DE 10 2004 045 770 B3 is, however, disadvantageous in so far as its cleaning performance is relatively limited and the dry ice consumption is relatively high. An increase in the cleaning performance of the apparatus in accordance with DE 10 2004 045 770 B3 would be possible by means of an increase in the quantity of propellant gas, which, however, would require a corresponding design and dimensioning of the compressed-air source with disadvantageous effects for the manageability of the apparatus. Furthermore, the apparatus in accordance with DE 10 2004 045 770 B3 is not suitable for topical and gentle applications such as cosmetic treatment or cleaning of the skin.

US-2006/0178092 A1 describes a cleaning device with a particle jet with a pressure vessel, in which the pressure is ordinarily used to convey the ice pellets, as explained inter alia in the abstract of US-2006/0178092 A1. The use of air as a conveying means is disadvantageous in so far as the device requires corresponding means for pressure generation and pressure conservation. Furthermore, in US-2006/0178092 A1, a grinding mechanism for comminution of ice pellets to a fixed size is described, which, however, has proved to be inadequate for numerous applications of the device in practice.

The invention is therefore based on the object of creating an apparatus and a method for surface processing or surface treatment by means of dry ice granulate which avoids the above-cited problems of the prior art.

Within the framework of this object, a particular object of the present invention is to provide an apparatus and a method for surface processing or surface treatment by means of dry ice granulate which increases the cleaning performance (aggressiveness) and at the same time lowers the consumption of dry ice granulate and/or the quantity of the propellant gas (transport air).

A further object of the invention is to create an apparatus and a method for surface processing or surface treatment by means of dry ice granulate which is suitable for topical and gentle applications such as cosmetic treatment or cleaning of the skin.

Moreover, a particular object of the present invention is to realise an apparatus and a method for surface processing or surface treatment by means of dry ice granulate which is easily and cost-effectively manufacturable.

The above objects and further objects, which can be seen from the following description, are fulfilled by an apparatus and a method in accordance with the appended main claims. Advantageous further developments of the present invention are the subject of the dependent claims.

BRIEF DESCRIPTION OF THE FIGURES

Further features and advantages of the present invention and the manner of action of the exemplary embodiment of the present invention are described below with reference to the accompanying drawings. The accompanying drawings illustrate the present invention and further serve, together with the description, to elucidate the basic principles of the invention and to enable a person skilled in the art of the field in question to manufacture and use the invention.

In them.

DESCRIPTION OF THE PREFERRED
EMBODIMENTS OF THE INVENTION

Figure 1:
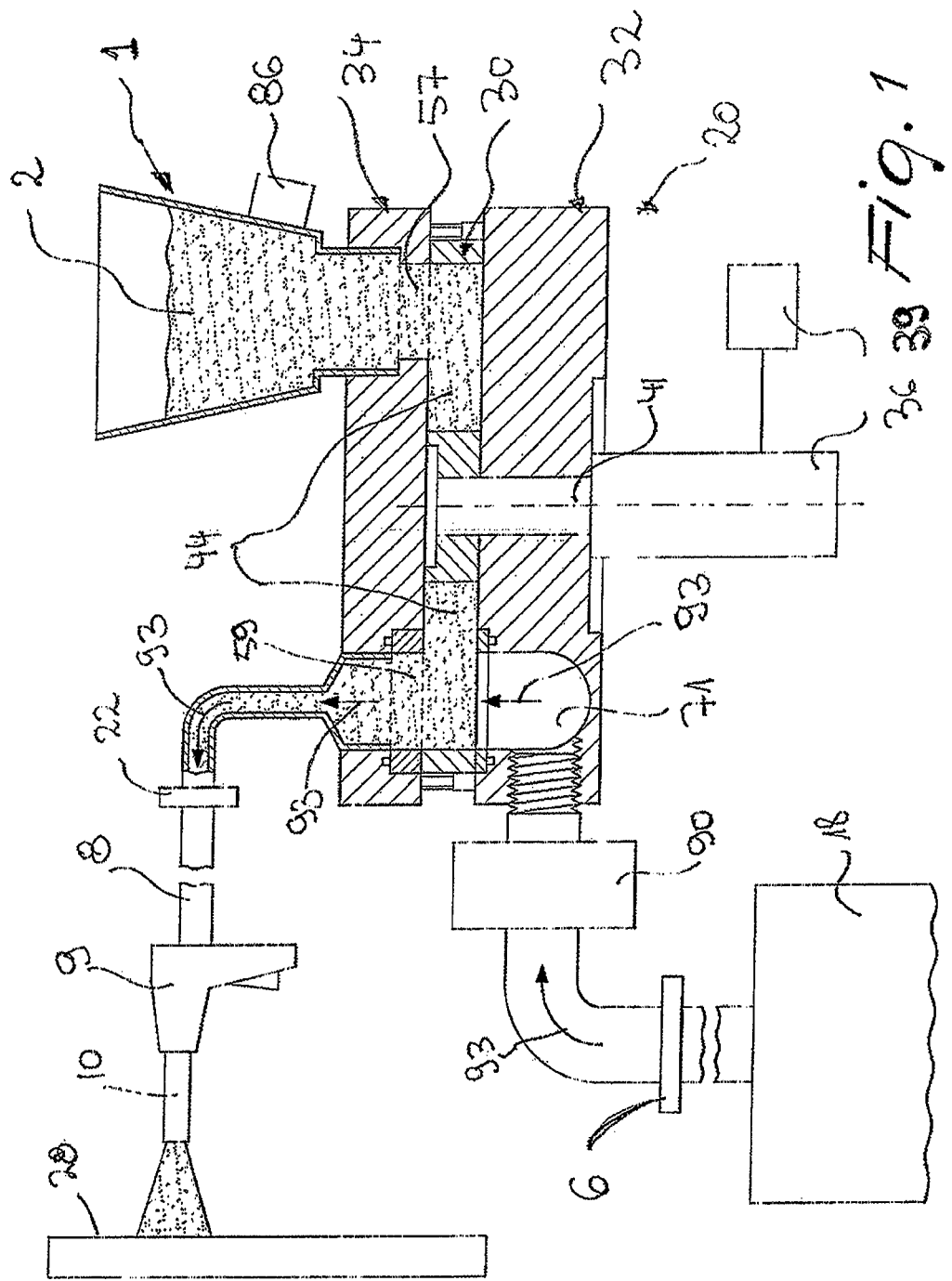
FIG. 1 shows a schematic representation of a known apparatus in accordance with DE 10 2004 045 770 B3.
Figure 2:
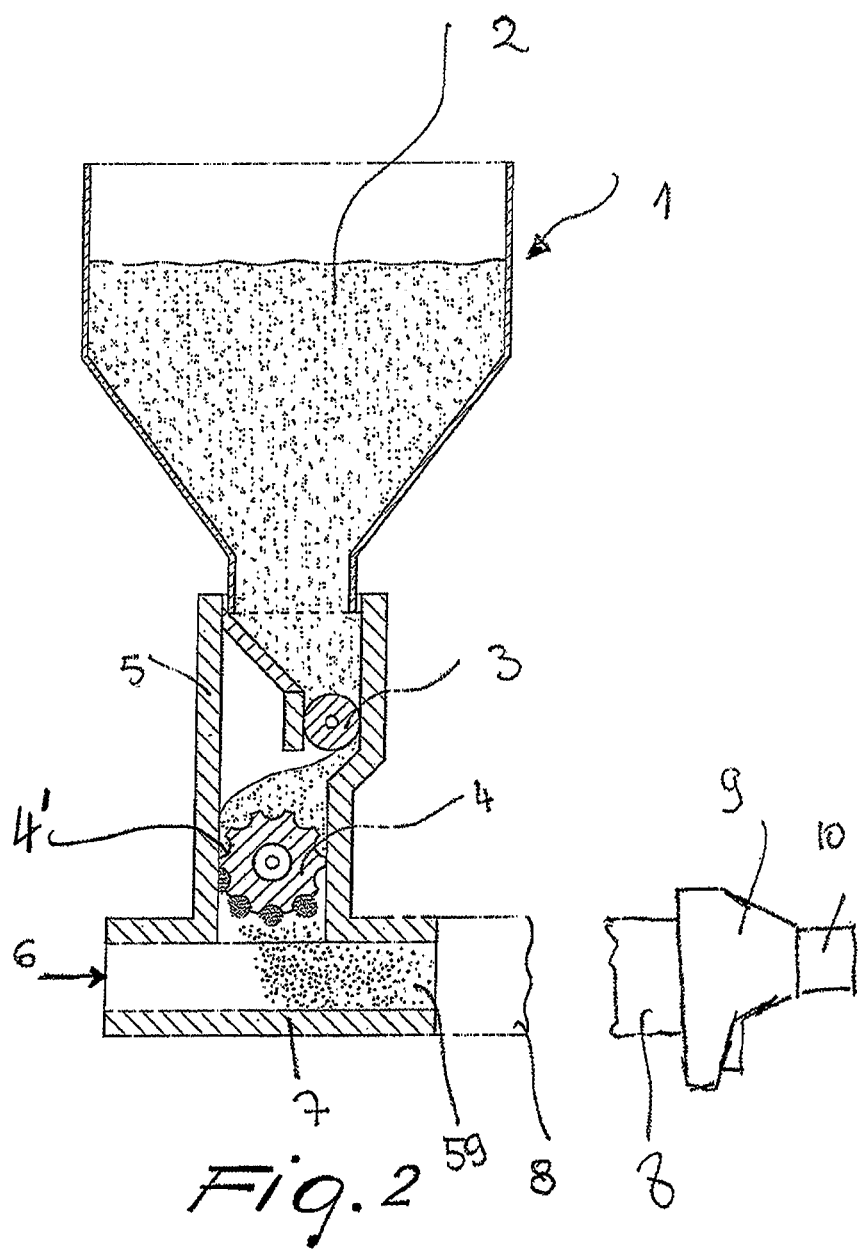
FIG. 2 shows a schematic representation of a first embodiment of the apparatus in accordance with the invention for surface processing or surface treatment by means of dry ice granulate.

With reference to FIG. 2, a schematic representation of a first embodiment of the apparatus in accordance with the invention for surface processing or surface treatment by means of dry ice granulate is explained, component parts in common with FIG. 1 being provided with like reference numerals.

The apparatus in accordance with the invention comprises an essentially funnel-shaped reservoir 1, which is filled with dry ice pellets (below, for simplification, referred to also as pellets). The pellets 2 have, as commercially available, a size of approximately 3 mm. The reservoir 1 can either be integrated in the apparatus, as shown in FIG. 1, or be coupled externally to the apparatus. The pellets 2 can be manufactured on site with an integrated apparatus (not shown) for production of dry ice granulate or be manufactured at an external site. It is, however, for the person skilled in the art, conceivable to operate the apparatus with further dry ice media, as long as the dry ice media can be comminuted to an adjustable comminution range, as given below.

In accordance with the invention, the reservoir 1 opens into a radially formed adjustable grinding mechanism 3, which comminutes the 3 mm pellets 2, resting on top due to gravity, into small particles, which lie in an adjustable range from approximately 0.5μ to approximately 2 mm Depending on the application, the comminution range of the pellets 2 can also lie in a region from approximately 100μ to approximately 1 mm or in a region from approximately 200μ to approximately 400μ, and preferably 300μ.

Advantageously, the radial grinding mechanism 3 is adapted so as to generate sharp-edged comminuted particles. The sharp-edgedness of the comminuted particles, which has the effect of assisting the cleaning performance, can be achieved by means of an adapted surface geometry of the crushing roll of the grinding mechanism 3. Particularly advantageously, the sharp-edged comminuted particles are formed octahedral.

The radial grinding mechanism 3 is driven rotationally by a motor, not shown, the quantity of the comminuted particles per unit time advantageously being variable by control of the speed of the motor or of the speed of the crushing roll of the grinding mechanism 3.

The comminuted particles from the grinding mechanism 3 strike, under the influence of gravity, a transport and metering roll 4 (below, more simply, designated also as transport roll), which preferably is formed radially and is provided with axially running notches 4'. The notches 4' preferably extend over the entire axial length of the transport roll 4. Furthermore, it is conceivable in accordance with the invention to realise circularly running notches (not shown) perpendicular to the axial notches 4'. Alternatively, the transport roll can also be realised with spirally running notches 4'. All types of notches can be realised as single compartments (chambers) or as a continuous structure.

The transport roll 4 is preferably likewise motorised in order to control its speed so that the quantity of the comminuted particles per unit time is varied.

As a result of the provision of the transport roll 4 in accordance with the invention, which is present in all embodiments described herein, the pressure vessel for conveying the comminuted particles, required in the prior art US-2006/0178092 A1, becomes dispensable in all embodiments of the invention. As shown in FIG. 2, the comminuted particles received into the notches are forced between the transport roll 4 and the vertical wall 5 of the feed chamber 57. Accordingly, it is conceivable in accordance with the invention to influence the shape or sharp-edgedness of the comminuted particles by means of the distance between the vertical wall 5 and the transport roll 5. This can be accomplished by means of a tulip- or funnel-shaped design (not shown) of the wall 5 and by means of a relative vertical displacement of the wall 5 and/or of the transport roll 4 in order thus to vary the distance therebetween.

As a result of the rotational motion of the transport roll 4, the comminuted particles fall into a flow channel 7, offset by 90°, of the apparatus in accordance with the invention, which channel 7 is, in a conventional manner, such as described in DE 10 2004 045 770 B3, loaded at the inlet 6 with compressed air by a compressed-air source 18. Due to the influence of compressed air, the comminuted particles pass into the transport hose 8 and from there into the blast gun 9 or rather into the Laval nozzle 10 of the blast gun 9. Instead of by compressed air, the comminuted particles can also be carried into the blast gun by means of a mixture of a gaseous phase (e.g. compressed air, nitrogen, $CO_2$) and/or a liquid phase (e.g. $CO_2$) and/or a solid phase (e.g. $CO_2$). For a person skilled in the art it will therefore be understood that the invention comprises all propellant media (propellant gases, propellant liquids or propelling solid phases) which are suitable for carrying the comminuted particles into the blast gun.

Figure 3:
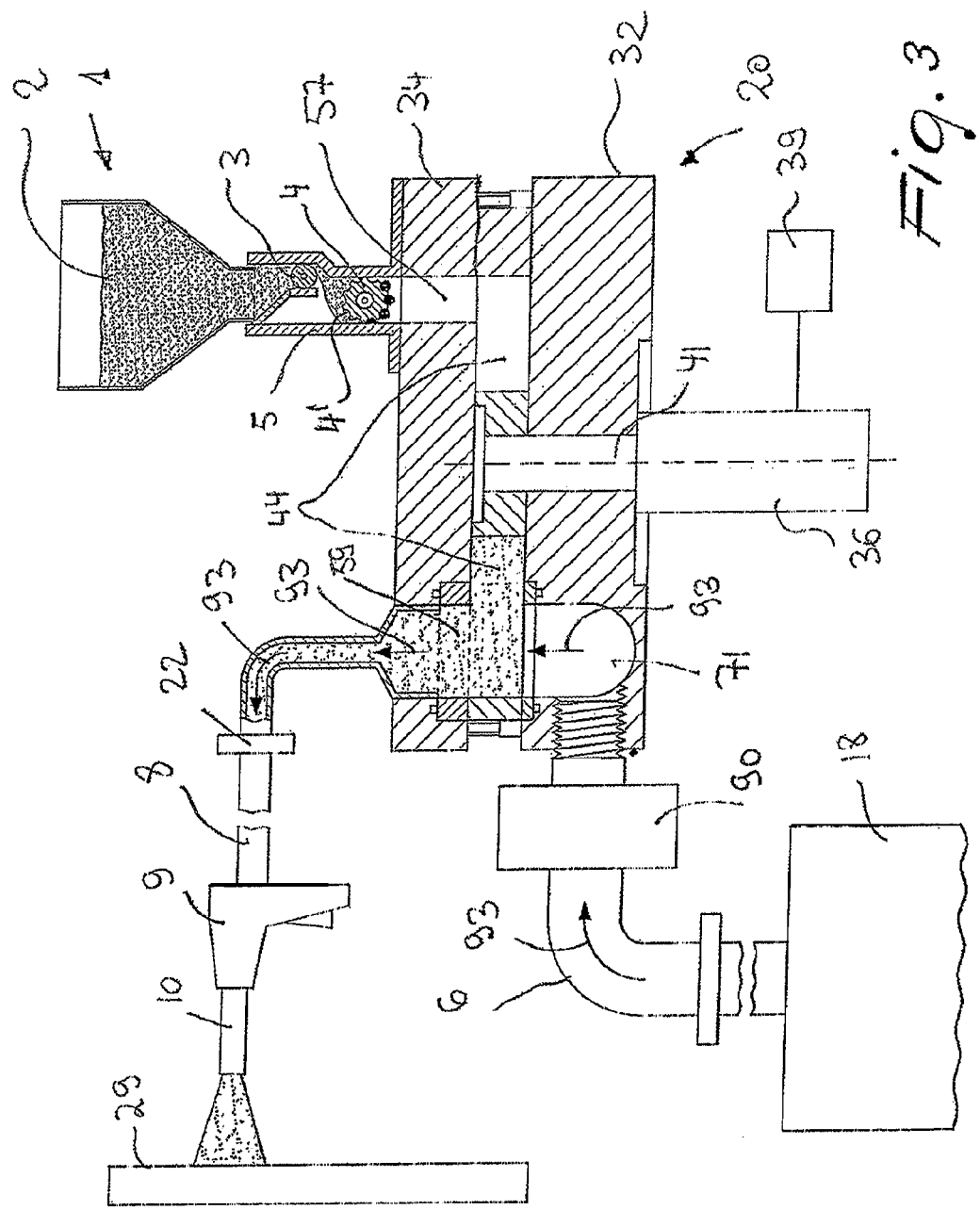
FIG. 3 shows a schematic representation of a second embodiment of the apparatus in accordance with the invention for surface processing or surface treatment by means of dry ice granulate.

With reference to FIG. 3, a schematic representation of a second embodiment of the apparatus in accordance with the invention for surface processing or surface treatment by means of dry ice granulate is explained, component parts in common with FIGS. 1 and 2 being provided with like reference numerals.

The second embodiment employs the reservoir 1, the grinding mechanism 3 and the transport roll 4 of the first embodiment in an apparatus 1, which is employed in conjunction with a metering device 20 of DE 10 2004 045 770 B3. By means of the latter combination, an additional adjustment of the quantity of the comminuted particles per unit time can be achieved particularly advantageously by control of the speed of the metering disc 30. Furthermore, the metering device 20 can be formed so as also to receive an additional medium (e.g. vitamins or anti-inflammatory agents in medical applications), it being possible to admix the additional medium with the particle jet.

In both the first and the second embodiment of the present invention, the adjustment of the quantity of the comminuted particles per unit time at the grinding mechanism and/or the transport roll and/or the metering device can be performed by means of one or more controllers (not shown) on the blast gun.

Figure 4:
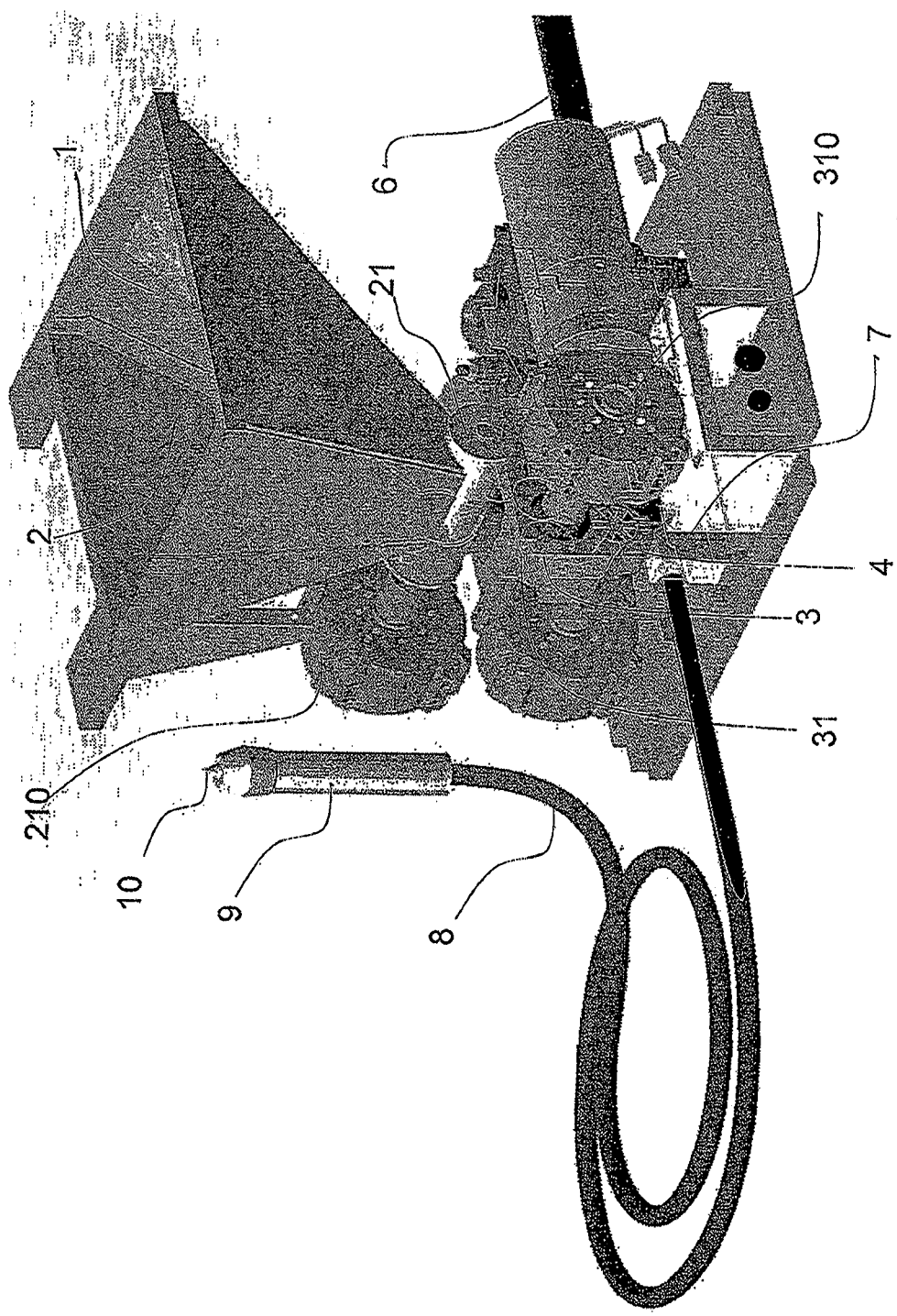
FIG. 4 shows a schematic perspective representation of a third embodiment of the apparatus in accordance with the invention for surface processing or surface treatment by means of dry ice granulate.

With reference to FIG. 4, a schematic representation of a third embodiment of the apparatus in accordance with the invention for surface processing or surface treatment by means of dry ice granulate is explained, component parts in common with FIGS. 1 and 3 being provided with like reference numerals.

In deviation from the first and the second embodiment, a conveying spiral 21 with spiral-shaped channels extending in the longitudinal direction is located downstream of the funnel-shaped reservoir 21 in order to feed the uncomminuted pellets 2 to the grinding mechanism 31 connected downstream. The conveying spiral 21 is driven in a known manner by means of a motor 210. The grinding mechanism 31 is driven by a further motor, indicated with the reference numeral 310.

The grinding mechanism 31 is formed with roll pairs so that, in deviation from the radial grinding mechanism 3 of the first and the second embodiment, in which the radial grinding mechanism 3 comminutes the pellets against the wall of the apparatus, the comminution takes place between the counter rotationally driven rolls of a respective roll pair. Although, in the third embodiment, the number of roll pairs is two, it can be changed as required. The roll pairs can be formed from cylindrical or truncated-conical rolls, and the variable distance between the rolls of each roll pair determines the comminution size of the pellets 2. A particularly advantageous design of a grinding mechanism 31 with truncated-conical rolls is explained below with reference to FIG. 5.

Downstream of the grinding mechanism 31, analogously to the first and the second embodiment of the invention, the transport and metering roll 4 is provided, from which the comminuted pellets 2 are transported by the compressed-air source 18 into the transport hose 8 and the blast gun 9.

Figure 5:
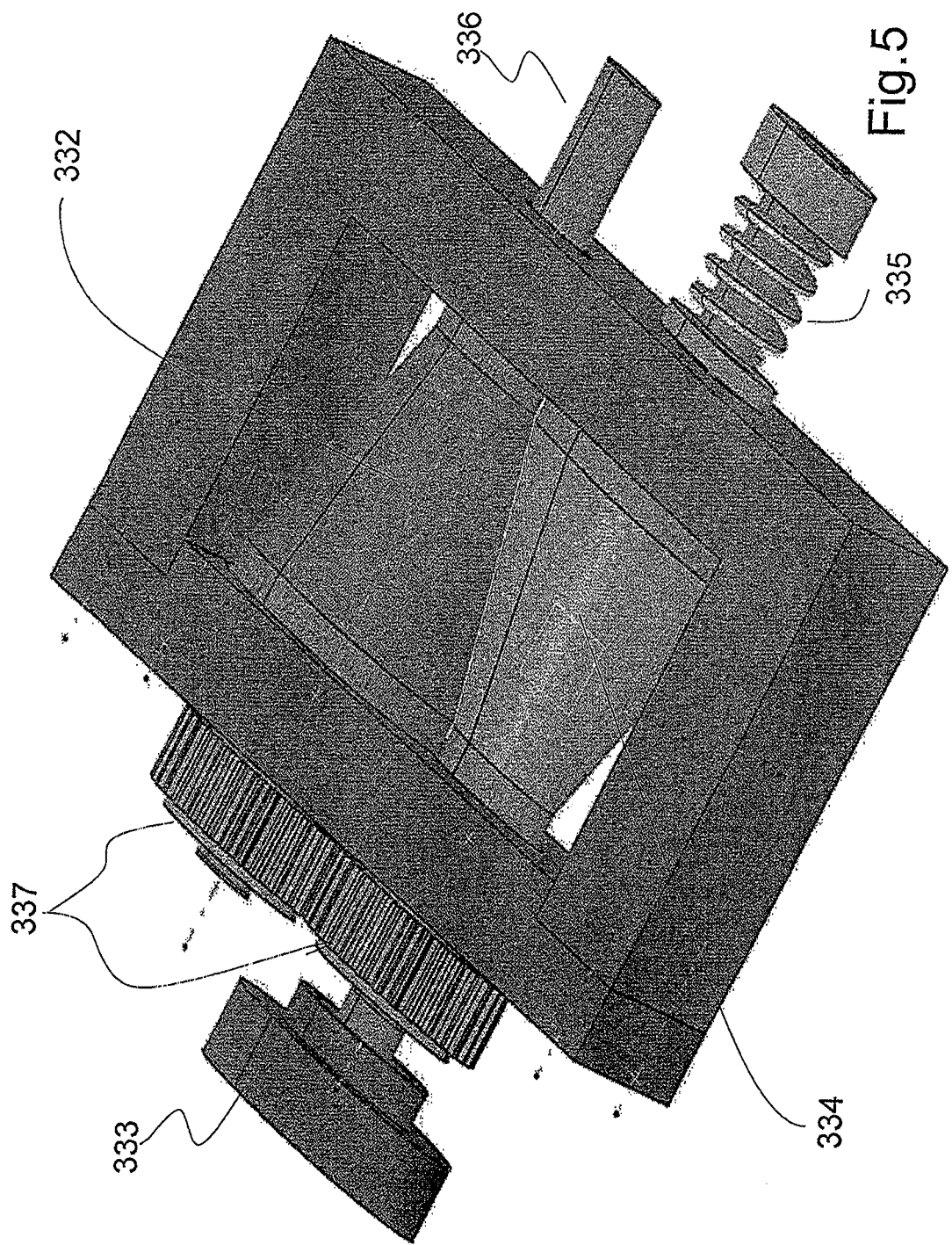
FIG. 5 shows a perspective schematic representation of a grinding mechanism which can be employed in conjunction with the first to third embodiments of the invention.

With reference to FIG. 5, an advantageous roll pair of a grinding mechanism is presented, which can be employed in all above-portrayed embodiments of the invention. The roll pair consists of a truncated-conical crushing roll 332 and a truncated-conical adjustable roll 334, which, by means of an adjusting wheel 333, is axially moveable against the action of a spring 335 in order to change the distance between the crushing and the adjustable roll. The counter rotational drive of the rolls takes place by means of a motor (not shown) connected to the shaft 336 and by means of the engagement of the gearwheels 337. The arrangement of FIG. 5 permits particularly advantageously a simple adjustment of the distance between the crushing and the adjustable roll, since the engagement of the gearwheels 337 is maintained over a certain axial length despite axial movement of the adjustable roll 334.

The above-described embodiments of the invention fulfill in full the objects set, in that an apparatus for surface processing or surface treatment by means of dry ice granulate is provided, which, by comminution of the 3 mm pellets, reduces the transport air volume by 50% with respect to the transport air volume which would be required to accelerate conventional pellets with the same exit speed, which typically lies in a range from approximately 200 m/s-300 m/s. Furthermore, as a result of the comminution in accordance with the invention, the effective quantity of granulated dry ice increases, which impinges 200-fold on the surface to be treated or to be processed, and thus the area performance can be drastically increased with respect to conventional apparatuses.

In accordance with the invention, a method for surface processing or surface treatment by means of dry ice granulate is also provided, which provides the comminution of the conventional 3 mm pellets to the aforementioned sizes before blasting of the surface to be treated or to be processed. Within the framework of the method, the dry ice granulate can be carried into the blast gun with compressed air and/or a mixture of a gaseous phase (e.g. compressed air, nitrogen, $CO_2$) and/or a liquid phase (e.g. $CO_2$).

Furthermore, the method in accordance with invention provides advantageous steps for adjusting the quantity of the comminuted particles per unit time at the grinding mechanism and/or the transport roll and/or the metering device. This can, as mentioned above, take place by means of one or more controllers (not shown) on the blast gun.

A further feature of the method in accordance with invention is the provision of steps for adjusting the shape or the sharp-edgedness of the comminuted particles, which steps, as mentioned above, can take place at the crushing roll of the grinding mechanism and/or at the transport roll.

The method in accordance with invention likewise fulfils the objects set and exhibits the same advantages which were explained in conjunction with the apparatus in accordance with the invention.

In addition, it was found, unexpectedly, by the present inventor that the method with application of the comminuted particles is very effective in the cosmetic treatment or cleaning of skin or dermabrasion, such as in the removal of tattoos, scars, in facelifting, peeling, resurfacing, partial tissue renewal and the like.

It was also found, unexpectedly, by the present inventor that the method with application of the comminuted particles is very effective in the treatment of diseases of the skin and of the subcutaneous tissue, and of the vascular bed and of other biological tissues which are accessible from outside, or those which can be laid open by operations or by means of an endoscopic technique.

In particular, the method in accordance with the invention has shown itself to be effective for selective abrasion of e.g. cells and tissues and for treatment of the undamaged skin surface by means of dynamic cold application (cyclically controlled intensity over time), and of benign and malign neoplasms, acute and chronic inflammatory diseases with and without infectious agents and chronic proliferative diseases, and also of healthy tissue (anti-aging), it being possible to select the diseases from the following group consisting of: benign keratoses, epitheliomas, dermatofibroma (eruptive), pyogenes granuloma, granuloma faciale, granuloma annulare, sarcoidosis, molluscum contagiosum, plane juvenile wart, vulgar warts, warts (plantar), papillomatis cutis, genital warts, condylomata acuminata, keloids, hypertrophic scars, acne vulgaris, hyperkeratosis, inflamed lesions and scars, shingles, LE (lupus erythematosus), leishmaniosis, haemangiomas, angiomas (eruptive), venous lake, syringoma, vascular naevi, Kaposi's sarcoma (acute), basal cell carcinoma (superficial), radiation keratoses (solar), Bowen's carcinoma, superficial carcinomas, relief therapy of skin or other tumour metastates, spider veins, lymphangiomas, haemangiomas, telangiectases, intraoral leukoplakia and in rheumatological disease forms and osteosis treatment by means of application of cold.

In the above-portrayed medical and cosmetic applications of the invention it is particularly advantageous if the fed dry ice pellets (or the dry ice medium) is sterilised, or are sterilised in the apparatus by means of correspondingly formed means. Alternatively or in addition thereto, the comminuted particles of the dry ice granulate also can be sterilised by means of correspondingly formed means integrated in the apparatus.

If technical features mentioned in any of the claims are provided with a reference numeral, these reference numerals have been included only to increase the understandability of the claims. Accordingly, these reference numerals have no limiting effect on the scope of protection of each element which is denoted by way of example by such reference numerals.

The invention claimed is:

1. Apparatus for surface processing or surface treatment by means of dry ice granulate, with a reservoir (1) for receiving a dry ice medium, in particular dry ice pellets, an inlet (6) for the feed of a propellant medium, an outlet (22) for the supply of a mixture of propellant medium and dry ice granulate to a blast gun (9), and an outflow chamber (59) lying therebetween, in which in a path between the reservoir (1) and the outflow chamber (59) there is arranged a grinding mechanism (3), which is formed so as to comminute the dry ice medium to dry ice granulate with a particle size in a prescribed range, the grinding mechanism (3) comprises a crushing roll, which is formed so as to give the particles of the dry ice granulate a sharp-edged shape, the grinding mechanism (3) is formed so as to adjust the size of the particles of the dry ice granulate variably in a range from approximately 2 mm to approximately 0.5μ, and a transport roll (4) is arranged between the grinding mechanism (3) and the outflow chamber (59), the transport roll (4) being operable with a variable speed so as to vary the quantity of the particles of the dry ice granulate per unit time, the apparatus further comprising a metering device (20), which is arranged between the transport roll (4) and the outflow chamber (59) and which is formed so as to vary the quantity of the particles of the dry ice granulate per unit time, the metering device (20) preferably being formed so as to receive an additional medium, which can be admixed with the particles of the dry ice granulate.

2. Apparatus for surface processing or surface treatment by means of dry ice granulate, with a reservoir (1) for receiving a dry ice medium, in particular dry ice pellets, an inlet (6) for the feed of a propellant medium, an outlet (22) for the supply of a mixture of propellant medium and dry ice granulate to a blast gun (9), and an outflow chamber (59) lying therebetween, in which in a path between the reservoir (1) and the outflow chamber (59) there is arranged a grinding mechanism (3), which is formed so as to comminute the dry ice medium to dry ice granulate with a particle size in a prescribed range, the grinding mechanism (3) comprises a crushing roll, which is formed so as to give the particles of the dry ice granulate a sharp-edged shape, the grinding mechanism (3) is formed so as to adjust the size of the particles of the dry ice granulate variably in a range from approximately 2 mm to approximately 0.5μ, the grinding mechanism (3) comprising at least one roll pair, the rolls of each pair being driven counter rotationally, and a transport roll (4) is arranged between the grinding mechanism (3) and the outflow chamber (59), the transport roll (4) being operable with a variable speed so as to vary the quantity of the particles of the dry ice granulate per unit time.

3. Apparatus in accordance with claim 2, in which the roll pair consists of a truncated-conical crushing roll (332) and a truncated-conical adjustable roll (334).

4. Apparatus in accordance with claim 3, in which the truncated-conical adjustable roll (334) roll is axially moveable by means of an adjusting wheel (333), which can be displaced manually or electrically, preferably by means of a stepper motor against the action of a spring (335), in order to change the distance between the crushing and the adjustable roll.

\* \* \* \* \*